United States Patent [19]

Puchalski, Jr. et al.

[11] Patent Number: 4,690,818

[45] Date of Patent: Sep. 1, 1987

[54] SHAMPOO AND BATH AND SHOWER GEL

[75] Inventors: Eugene Puchalski, Jr., Jersey City; Emil F. Schneider, Long Branch; Judith A. Cohee, Atlantic Highlands; El-Sayed El-Menshawy, Holmdel, all of N.J.

[73] Assignee: Charles of the Ritz Group Ltd., New York, N.Y.

[21] Appl. No.: 825,169

[22] Filed: Feb. 3, 1986

[51] Int. Cl.$^4$ .............................................. A61K 7/06
[52] U.S. Cl. ...................................... 424/70; 514/944
[58] Field of Search ........................... 424/70; 514/944

[56] References Cited

FOREIGN PATENT DOCUMENTS 0101887 3/1984 European Pat. Off. .............. 424/69

OTHER PUBLICATIONS

Cosmetics & Toiletries (I) 3/1984, vol. 99, pp. 66 to 68, 70 to 72.
Cosmetics & Toiletries (II) 4/1985, vol. 100, pp. 36 57, 84, 88, 90 to 92, 94 and 95.
Chemisches Laboratorium, Dr. Kurt Richter GmbH, West Berlin Company Brochure on Hygroplex HHG No. 18.
Company Brochure on "The Moisture Principle.".
Company Brochure on "Evaluation of the Preparation of Hygroplex HHG.
Croda, Inc., Brochure on Croquat L, M & S.

*Primary Examiner*—Dale R. Ore
*Attorney, Agent, or Firm*—Lerner, David, Littenberg, Krumholz & Mentlik

[57] ABSTRACT

A cleansing composition which may be in the form of a shampoo and/or bath and shower gel is provided which includes a unique combination of hair and skin conditioners and moisturizers, namely, a combination of cocodimonium hydrolyzed keratin and a mixture of monosaccharides and disaccharides in natural combination with amino acids.

15 Claims, No Drawings

SHAMPOO AND BATH AND SHOWER GEL

FIELD OF THE INVENTION

The present invention relates to a shampoo, and bath and shower gel which have improved substantivity and leave a conditioning film on hair, scalp and skin.

DESCRIPTION OF THE INVENTION

In accordance with the present invention there is provided a shampoo and/or bath and shower gel which have unexpectedly good substantivity. When the invention is in the form of a shampoo, the shampoo imparts good manageability, lustre (shine), and conditioning, and anti-static properties to the hair. When the shampoo is rinsed from the hair, cleansers are removed while those components which impart the above benefits remain for up to 24 hours and more. When the invention is in the form of a bath and shower gel, the gel conditions the skin and continues to do so even after the cleansers have been washed from the skin.

The unique substantivity properties of the shampoo and/or bath and shower gel of the invention, hereinafter referred to as the composition of the invention, are provided by including a unique combination of hair and skin conditioners and moisturizers, namely, a combination of cocodimonium hydrolyzed keratin and a mixture of monosaccharides and disaccharides in natural combination with amino acids. In addition, the shampoo and/or bath and shower gel will contain water, one or more acids to adjust pH to within the range of from about 0.001 to about 0.5, one or more thickeners, one or more cleansers and/or detergents, optionally one or more additional conditioners, optionally one or more proteins for protecting hair, optionally one or more emollients and/or humectants, optionally one or more chelating agents to remove metals and soften water, optionally one or more preservatives, optionally one or more viscosity adjusters and/or feel enhancers, optionally one or more fragrances and optionally one or more coloring agents.

As indicated, the composition of the invention includes a unique combination of ingredients that aids in forming a long-lasting hair and skin-conditioning film, which combination includes (A) cocodimonium hydrolyzed keratin and (B) a mixture of monosaccharides and disaccharides in natural combination with amino acids which combination will include a weight ratio of (A) to (B) of within the range of from about 0.001:1 to about 5:1 and preferably from about 0.5:1 to about 2:1, and optimally from about 1:1 to about 2:1.

The cocodimonium hydrolyzed keratin will be present in the composition of the invention in an amount of within the range of from about 0.05 to about 2% and preferably from about 0.1 to about 1.66% by weight of the total composition. An example of such compound in commercially available form is Croquat KM, a trademark of Croda Inc., New York City. Croquat KM (cocodimonium hydrolyzed keratin) is a quaternized protein based on the keratin protein. Normal proteins are only substantive below their isoelectric point which limits their cationic character; by quaternizing hydrolyzed animal protein or collagen hydrolysate (for example, Crotein, trademark of Croda), it allows it to retain its charge thus allowing it to form strong ionic bonds to skin at all pH's up to pH 10. Substantivity studies have shown the quaternized proteins to be conditioning and film forming at lower concentrations.

The mixture of monosaccharides and disaccharies in natural combination with amino acids will be present in the composition of the invention in an amount within the range of from about 0.001 to about 5%, and preferably from about 0.1 to about 2.5% by weight of the total composition, and may be obtained commercially under the name Hygroplex HHG, trademark of Chemisches Laboratorium Dr. Kurt Richter GmbH, West Berlin, which is formed of hexylene glycol, glucose, fructose, sucrose, urea, dextrin, alanine, glutinic acid, aspartic acid and hexyl nicotinate. Hygroplex HHG resembles the natural moisturizing factors in skin composition and protects the skin from moisture loss or acts to replace the natural moisturizing factors. Hygroplex HHG has the same water binding capacity as human skin.

A chelating agent will be present in the composition of the invention to remove metals and thus soften water used during washing of the hair and/or skin. The chelating agent will be present in an amount within the range of from about 0.001 to about 0.5% and preferably from about 0.05 to about 0.1% by weight of the composition, examples of which include disodium ethylenediamine tetraacetic acid (such as Sequestrene No. 2, trademark of Ciba-Geigy), or tetrasodium ethylenediamine tetraacetic acid (such as Sequestrene No. 4, Ciba-Geigy).

As indicated, the composition of the invention will also include an acid to adjust and/or maintain pH of the composition within the range of from about 0.001 to about 0.3. Examples of suitable acids include citric acid, ascorbic acid, lactic acid or phosphoric acid employed in amounts within the range of from about 0.001 to about 0.5% and preferably from about 0.05 to about 0.15% by weight of the composition.

One or more humectants and/or emollients may also be employed in amounts within the range of from about 0.001 to about 5%, and preferably from about 0.5 to about 2% by weight, examples of which include hexylene glycol, PEG-7 glyceryl cocoate (Cetrol HE, Henkel), propylene glycol or sorbitol, sodium pyrrolidonecarboxylic acid (Ajidew N-50, Ajinomoto), glycerine or polyethylene glycol wax, such as Carbowax 400.

Detergents and/or cleansers may be present in amounts within the range of from about 5% to about 60% and preferably from about 35% to about 50% by weight of the composition. Examples of such detergents or cleansers include sodium laureth sulfate (Standapol ES-1, trademark of Henkel), ammonium laureth sulfate, triethanolamine laureth sulfate (Onyx Chem.), monocarboxylic coconut derivative (Amphoteric, Miranol) or $NaC_{14}-C_{16}$ olefin sulphonate (Bioterge AS-40, Stephen Chem).

Additives to promote good feel and/or adjust viscosity may optionally be present in an amount within the range of from about 0.001 to about 1% and preferably from about 0.05 to about 0.75% by weight. Examples of feel enhancers and/or viscosity adjusters include PEG 120 methyl glycoside dioleate (Glucamate DOE-120), coconut and lauric amino pyropyl betaines, PEG-7-cocoate or Quaternium 70.

The composition of the invention will also preferably include a hydrolyzed animal protein to protect hair and enhance skin feel and promote formation of a water-soluble film, in an amount of within the range of from about 0.01 to about 5% and preferably from about 0.15 to about 1.5% by weight of the composition. The hydrolyzed animal protein will preferably be myristolyl hydrolyzed animal protein such as Lexein A-210, trademark of Inolex Chemicals, which normally is supplied in an ethanol solution or Crotein SPA, trademark of Croda.

The composition of the invention may optionally include from 0 to about 1.5% and preferably from about 0.1 to about 1% by weight of a preservative, such as imidazolidinyl urea (for example, Germall 115), methyl or propyl paraben, dimethyldimethoyl hydantoin, Dowicil 200 (Quaternium 15), that is, N-(3-chloroallyl)-hexaminium chloride, benzyl alcohol and/or phenoxyethanol, with imidazolidinyl urea and methyl paraben being preferred.

Water will be employed in the composition of the invention as a solvent and carrier and will be present in an amount within the range of from about 10 to about 60% and preferably from about 15 to about 50% by weight.

A polyol to enhance skin feel may be present in an amount within the range of from about 0.1 to about 10% and preferably from about 0.2 to about 4% by weight. Examples of such polyols (which will also serve as humectants) suitable for use herein include, but are not limited to, polyethylene glycol (for example, PEG 8), sorbitol, glycerin, polyoxyethylene (26) glyceryl ether (Liponic EG1), propylene glycol, 1,3-butylene glycol or hexylene glycol with polyoxyethylene (26) glyceryl ether being preferred.

The composition of the invention may optionally include a thickener in an amount within the range of from 0 to about 5% and preferably from about 0.05 to about 4% by weight. A preferred thickener suitable for use herein is Cocamide DEA (a mixture of ethanolamides of coconut acid) also referred to as Standamid SD (trademark of Henkel). Carbopol 940 or Carbomer 940 which is hydrophilic acrylic polymer cross-linked with a polyfunctional agent and employed with an organic or inorganic base, preferably triethanolamine, may also be used. Other examples of thickeners which may be employed herein include, but are not limited to, hydroxyethyl cellulose, hydroxy propylcellulose or xanthan gum, etc.

Other hair and skin conditioning agents which may optionally be present in the composition of the invention include allantoin, d- or dl-panthenol, sodium-2-pyrrolidone carboxylic acid, Quaternium 70 (Ceraphyl 70, trademark of Van Dyk Chemical), cocoamidopropyl betaine (Velvetex BA-35, trademark of Henkel, Inc.) and the like. Such conditioning agents mend split hair ends and protect the skin and may be present in an amount within the range of from about 0.01 to about 5% and preferably from about 0.05 to about 2% by weight.

In addition to the ingredients set out above, the composition of the invention may include certified water-soluble colorants as deemed necessary and fragrances in amounts within the range of from about 0 to about 10% and preferably from about 0.1 to about 5% by weight.

The composition of the invention may also optionally include from 0 to about 10% by weight of one or more sun screen agents such as octyl dimethyl p-aminobenzoic acid or benzophenone 3 (Uvinul D-50).

Preferred formulations in accordance with the present invention are set out below.

| Ingredient | % by Weight |
|---|---|
| Cocodimonium hydrolyzed keratin | 0.001 to 5 |
| Mixture of mono- and di-saccharides with amino acids | 0.001 to 5 |
| Acids (e.g. citric acid) | 0.001 to 0.3 |
| Thickeners (e.g. cocoamide DEA) | 0 to 5 |
| Detergent (or cleansers) (e.g. Na Laureth sulfate) | 15 to 50 |
| Additional conditioners (e.g. panthenol, Ceraphyl 70 and Velvetex BA-35) | 0.001 to 10 |
| Proteins (e.g. hydrolyzed animal protein) | 0.01 to 1.5 |
| Emollients and/or humectants (e.g. hexylene glycol and Na PCA) | 0.01 to 10 |
| Chelating agents (e.g. DiNa EDTA) | 0.05 to 0.5 |
| Viscosity adjusters and/or feel enhancers (e.g. PEG 120 methyl glycoside dioleate) | 0.01 to 10 |
| Water | 15 to 50 |
| Preservatives | 0 to 1.5 |

The compositions of the invention when applied to the skin have surprisingly high substantivity, that is, they remain on the skin and hair for extended periods of time providing the desired and needed skin and hair conditioning and moisturizing.

The compositions of the invention containing the unique substantive film forming combination as set out above can be prepared as follows:

Water is heated to a temperature of from about 65° to 75° C., at which time protein, chelating agents, preservative, water-soluble humectant, such as Na PCA and hexylene glycol, acid, conditioner, such as dl-panthenol, are added with propeller mixing. Thereafter, conditioner such as Ceraphyl 70, and viscosity adjuster and feel enhancer, such as PEG 120 methyl glycoside dioleate, are added with propeller mixing while heating to 65° to 75° C. When a uniform mixture is obtained, sweep mixing is commenced and then conditioner and detergent are slowly added one at a time. Thereafter, a mixture of thickener and emollient, and cocodimonium hydrolyzed keratin (Croquat KM) and mixture of mono- and di-saccharides with amino acid (Hygroplex HHG) are added with propeller mixing 45°–50° to form the composition of the invention.

The following Examples represent preferred embodiments of the invention. All temperatures are expressed in degrees Centigrade.

EXAMPLE 1

A hair conditioning shampoo composition in accordance with the present invention having the following composition was prepared as described below.

| Ingredient | Parts by Weight |
|---|---|
| Phase A | |
| Deionized water | 45 |
| Hydrolyzed animal protein (Crotein SPA for hair protection) | 0.5 |
| DiNa EDTA (chelating agent) | 0.1 |
| Methyl paraben (preservative) | 0.1 |
| Na PCA (Ajidew N-50) (humectant) | 0.5 |
| Dimethyldimethoyl hydrantoin (Glydant 55%) (preservative) | 0.2 |
| Citric acid (pH adjuster) | 0.2 |
| dl-Panthenol (hair conditioner) | 0.5 |
| Hexylene glycol (humectant) | 0.001 |
| Phase B | |

| Ingredient | Parts by Weight |
| --- | --- |
| Quaternium 70 (Ceraphyl 70-conditioner) | 0.2 |
| PEG 120 methyl glycoside dioleate (viscosity adjuster) | 0.2 |
| Phase C | |
| Cocoamidopropyl betaine (conditioner) | 7 |
| Na laureth sulfate (detergent and cleanser) | 40 |
| Phase D | |
| Cocoamide DEA (diethanolamide, thickener) | 3 |
| PEG 7 Glyceryl cocoate (emollient) | 1 |
| Hygroplex HHG (moisturizer | 0.5 |
| Croquat KM   combination) | 0.4 |
| Fragrance | 1 |

Water was heated to a temperature of from about 65° to 75° C., at which time Phase A ingredients, namely, protein, chelating agents, preservative, water-soluble humectant, namely, Na PCA and hexylene glycol, acid, conditioner, namely, dl-panthenol, were added with propeller mixing. Thereafter, Phase B ingredients, namely, conditioner such as Ceraphyl 70, and viscosity adjuster and feel enhancer, such as PEG 120 methyl glycoside dioleate, were added with propeller mixing while heating to 65° to 75° C. When a uniform mixture was obtained, sweep mixing was commenced and then Phase C ingredients, namely, conditioner and detergent were slowly added one at a time. Thereafter, Phase D ingredients, namely, a mixture of thickener and emollient, and cocodimonium hydrolyzed keratin (Croquat KM) and mixture of mono- and di-saccharides with amino acid (Hygroplex HHG) were added with propeller mixing at 45°-50° C. to form the shampoo composition of the invention. The so-formed shampoo had excellent substantivity and moisturizing properties. Upon rinsing, soapy or cleansing materials were removed, but the unique moisturizer combination remained on the hair and scalp to provide manageability, lustre and conditioning.

EXAMPLE 2

A bath and shower gel composition in accordance with the present invention having the following composition was prepared as described below.

| Ingredient | Parts by Weight |
| --- | --- |
| Phase A | |
| Deionized water | 46.7 |
| Hydrolyzed animal protein (Crotein SPA for hair protection) | 0.5 |
| DiNa EDTA (chelating agent) | 0.1 |
| Methyl paraben (preservative) | 0.1 |
| Na PCA (Ajidew N-50) (humectant) | 0.5 |
| Dimethyldimethoyl hydrantoin (Glydant 55%) (preservative) | 0.2 |
| Citric acid (pH adjuster) | 0.2 |
| dl-Panthenol (hair conditioner) | 0.4 |
| Hexylene glycol (humectant) | 0.001 |
| Hygroplex HHG | 0.5 |
| Phase B | |
| Quaternium 70 (Ceraphyl 70-conditioner) | 0.2 |
| PEG 120 methyl glycoside dioleate (viscosity adjuster) | 0.2 |
| Phase C | |
| Cocoamidopropyl betaine | 5 |
| (conditioner) | |
| Na laureth sulfate (detergent and cleanser) | 40 |
| Phase D | |
| Cocoamide DEA (diethanolamide, thickener) | 3 |
| PEG 7 Glyceryl cocoate (emollient) | 1 |
| Hygroplex HHG (moisturizer | 0.5 |
| Croquat K   combination) | 0.5 |
| Fragrance | 0.4 |

Water was heated to a temperature of from about 65° to 75° C., at which time Phase A ingredients, namely, protein, chelating agents, preservative, water-soluble humectant, namely, Na PCA and hexylene glycol, acid, conditioner, namely, dl-panthenol, were added with propeller mixing. Thereafter, Phase B ingredients, namely, conditioner such as Ceraphyl 70, and viscosity adjuster and feel enhancer, such as PEG 120 methyl glycoside dioleate and Hygroplex HHG mixture of mono- and di-saccharides with amino acids, were added with propeller mixing while heating to 65° to 75° C. When a uniform mixture was obtained, sweep mixing was commenced and then Phase C ingredients, namely, conditioner and detergent were slowly added one at a time. Thereafter, Phase D ingredients, namely, a mixture of thickener and emollient, and cocodimonium hydrolyzed keratin (Croquat KM), Hygroplex HHG, were added with propeller mixing at 45°-50° C. to form the bath and shower gel composition of the invention.

The so-formed bath and shower gel had excellent substantivity, moisturizing and skin conditioning properties.

What is claimed is:

1. A shampoo or bath and shower gel composition having excellent conditioning and moisturizing properties and substantivity comprising a combination of from about 0.05 to about 2% by weight of (A) cocodimonium hydrolyzed keratin, and from about 0.001 to about 5% by weight of (B) a mixture of monosaccharides and disaccharides in natural combination with amino acids which includes hexylene glycol, glucose, fructose, sucrose, urea, dextrin, alanine, glutinic acid, aspartic acid and hexyl nicotinate in a wt. ratio of (A) to (B) within the range of from about 0.001:1 to about 5:1, and from about 10 to about 60% by weight water, from 0 to about 5% by weight thickener, from 5% to about 60% by weight cleanser or detergent, from 0.001 to about 0.5% by weight acid to adjust pH to appropriate levels, from 0.001 to about 0.5% by weight chelating agent, from 0.01 to about 5% by weight of conditioner, preservative, from 0.001 to about 1% by weight viscosity adjuster or feel enhancer, from about 0.01 to about 5% by weight of hydrolyzed animal protein, and from 0.001 to about 5% by weight humectant or emollient.

2. The composition as defined in claim 1 in the form of a shampoo.

3. The composition as defined in claim 1 in the form of a bath and shower gel.

4. The composition as defined in claim 1 wherein the cocodimonium hydrolyzed keratin is present in an amount within the range of from about 0.05 to about 1% by weight and the mixture of monosaccharides and disaccharides with amino acids is present in an amount within the range of from about 0.05 to about 1% by weight.

5. The composition as defined in claim 1 further including chelating agent.

6. The composition as defined in claim 7 wherein the chelating agent is DiNA ethylenediamine tetraacetic acid.

7. The composition as defined in claim 1 further including conditioners which include dl-panthenol, allantoin and cocoamidopropyl betaine.

8. The composition as defined in claim 1 wherein the thickener is cocoamido-diethanolamide.

9. The composition as defined in claim 1 wherein the cleanser is Na laureth sulfate.

10. The composition as defined in claim 1 further including preservative.

11. The composition as defined in claim 9 wherein the preservative is methyl paraben and dimethyl dimethoyl hydantoin.

12. The composition as defined in claim 1 wherein the acid is citric acid to adjust pH within the range of from about 0.01 to about 0.3.

13. The composition as defined in claim 1 further including humectant or emollient.

14. The composition as defined in claim 13 wherein the humectant is hexylene glycol, PEG 7 glyceryl cocoate or Na pyrrolidone carboxylic acid.

15. The composition as defined in claim 1 containing from about 0.05 to about 1% cocodimonium hydrolyzed keratin, from about 0.05 to about 1% mixture of mono- and di-saccharides with amino acids, from about 0.05 to about 0.3% acid to adjust pH, from about 0.01 to about 5% thickener, from about 35 to about 50% detergent or cleanser, from about 0.01 to about 10% additional conditioner, from about 0.01 to about 1.5% hydrolyzed animal protein, from about 0.01 to about 10% emollient or humectant, from about 0.01 to about 0.5% chelating agent, from about 0.01 to about 1.5% preservative and from about 15 to about 50% water.

* * * * *